(12) United States Patent
Shurnas (10) Patent No.: US 7,901,431 B2
(45) Date of Patent: Mar. 8, 2011

(54) LISFRANC REPAIR USING SUTURE-BUTTON CONSTRUCT

(75) Inventor: Paul J. Shurnas, Columbia, MO (US)

(73) Assignee: Arthrex, Inc., Naples, FL (US)

( * ) Notice: Subject to any disclaimer, the term of this patent is extended or adjusted under 35 U.S.C. 154(b) by 582 days.

(21) Appl. No.: 12/016,121

(22) Filed: Jan. 17, 2008

(65) Prior Publication Data

US 2008/0177302 A1   Jul. 24, 2008

Related U.S. Application Data

(60) Provisional application No. 60/880,704, filed on Jan. 17, 2007.

(51) Int. Cl.
*A61B 17/04* (2006.01)
*A61B 17/84* (2006.01)
*A61F 2/08* (2006.01)

(52) U.S. Cl. ............... 606/232; 606/300; 623/13.11

(58) Field of Classification Search ............... 623/21.19, 623/908, 13.11; 128/898; 606/232, 300, 606/86 R, 96, 60, 254, 255, 260, 263
See application file for complete search history.

(56) References Cited

U.S. PATENT DOCUMENTS

| | | | | |
|---|---|---|---|---|
| 5,219,359 | A * | 6/1993 | McQuilkin et al. | 606/232 |
| 5,306,301 | A * | 4/1994 | Graf et al. | 606/232 |
| 5,529,075 | A * | 6/1996 | Clark | 128/898 |
| 5,601,565 | A * | 2/1997 | Huebner | 606/87 |
| 6,099,568 | A * | 8/2000 | Simonian et al. | 623/13.11 |
| 6,117,160 | A * | 9/2000 | Bonutti | 606/215 |
| 6,533,802 | B2 * | 3/2003 | Bojarski et al. | 606/232 |
| 6,635,074 | B2 * | 10/2003 | Bartlett | 606/232 |
| 6,719,801 | B1 * | 4/2004 | Holt | 623/21.11 |
| 6,964,645 | B1 * | 11/2005 | Smits | 602/30 |
| 7,235,091 | B2 * | 6/2007 | Thornes | 606/232 |

(Continued)

FOREIGN PATENT DOCUMENTS

WO   WO2009/018527   *   2/2009

OTHER PUBLICATIONS

Huber et al., The Mitek Mini Anchor in the Treatment of Gamekeeper's Thumb, 1997, Eurepean Journal of Plastic Surgery, 20:251-255.*

(Continued)

*Primary Examiner* — Darwin P Erezo
*Assistant Examiner* — Dianne Dornbusch
(74) *Attorney, Agent, or Firm* — Dickstein Shapiro LLP (57) ABSTRACT

An apparatus and method for Lisfranc repair using a suture-button construct. The method includes the steps of drilling a hole in a medial cuneiform and through a second metatarsal base, passing a needle with a pull-through suture strand through the hole, pulling the pull-through suture strand and simultaneously applying a lateral tension on a first suture strand such that the first button lies sideways and advancing the first button through the hole until the it exits the hole at the medial cuneiform, flipping the first button to engage it against the medial aspect of the medial cuneiform and applying a lateral tension on the first suture strand, pulling free ends of the first suture strand to advance a second button over the second metatarsal base and to engage it against the second metatarsal base, and securing the second button against the second metatarsal base by tying a Surgeon's knot and two reverse half-hitches.

5 Claims, 10 Drawing Sheets

U.S. PATENT DOCUMENTS

| | | | |
|---|---|---|---|
| 7,344,538 B2* | 3/2008 | Myerson et al. | 606/280 |
| 7,530,990 B2* | 5/2009 | Perriello et al. | 606/232 |
| 2002/0077631 A1* | 6/2002 | Lubbers et al. | 606/72 |
| 2003/0023268 A1* | 1/2003 | Lizardi | 606/232 |
| 2003/0236555 A1* | 12/2003 | Thornes | 606/232 |
| 2006/0178702 A1* | 8/2006 | Pierce et al. | 606/232 |
| 2006/0206044 A1* | 9/2006 | Simon | 602/23 |
| 2006/0235397 A1* | 10/2006 | Sanders et al. | 606/69 |
| 2008/0208252 A1* | 8/2008 | Holmes | 606/232 |
| 2008/0287991 A1* | 11/2008 | Fromm | 606/232 |
| 2009/0036893 A1* | 2/2009 | Kartalian et al. | 606/60 |
| 2010/0152752 A1* | 6/2010 | Denove et al. | 606/148 |
| 2010/0211071 A1* | 8/2010 | Lettmann et al. | 606/60 |
| 2010/0217328 A1* | 8/2010 | Terrill et al. | 606/286 |
| 2010/0268273 A1* | 10/2010 | Albertorio et al. | 606/232 |

OTHER PUBLICATIONS

James W. Miller, M.D. Distal First Metatarsal Displacement Osteotomy: Its place in the Schema of Bunion Surgery, 1975, The Journal of Bone and Joint Surgery, 56: 923-931.*

H. Kelikiam, M.D. Hallux Valgus, Allied Deformities of the Forefootand Metatarsalgia, 1965, W.B. Saunders Company, pp. 253-256.*

* cited by examiner

LISFRANC REPAIR USING SUTURE-BUTTON CONSTRUCT

CROSS REFERENCE TO RELATED APPLICATIONS

This application claims priority to U.S. Provisional Application No. 60/880,704, filed on Jan. 17, 2007, the entire disclosure of which is hereby incorporated by reference.

BACKGROUND OF THE INVENTION

1. Field of the Invention

The present invention relates to the field of surgery and, in particular, to a Lisfranc repair technique using a suture-button construct and a device.

2. Description of the Related Art

Lisfranc injury is an injury to one of the small joints of the midfoot. The injury occurs when there is a dislocation or fracture and dislocation between the forefoot and midfoot joints.

Figure 1:
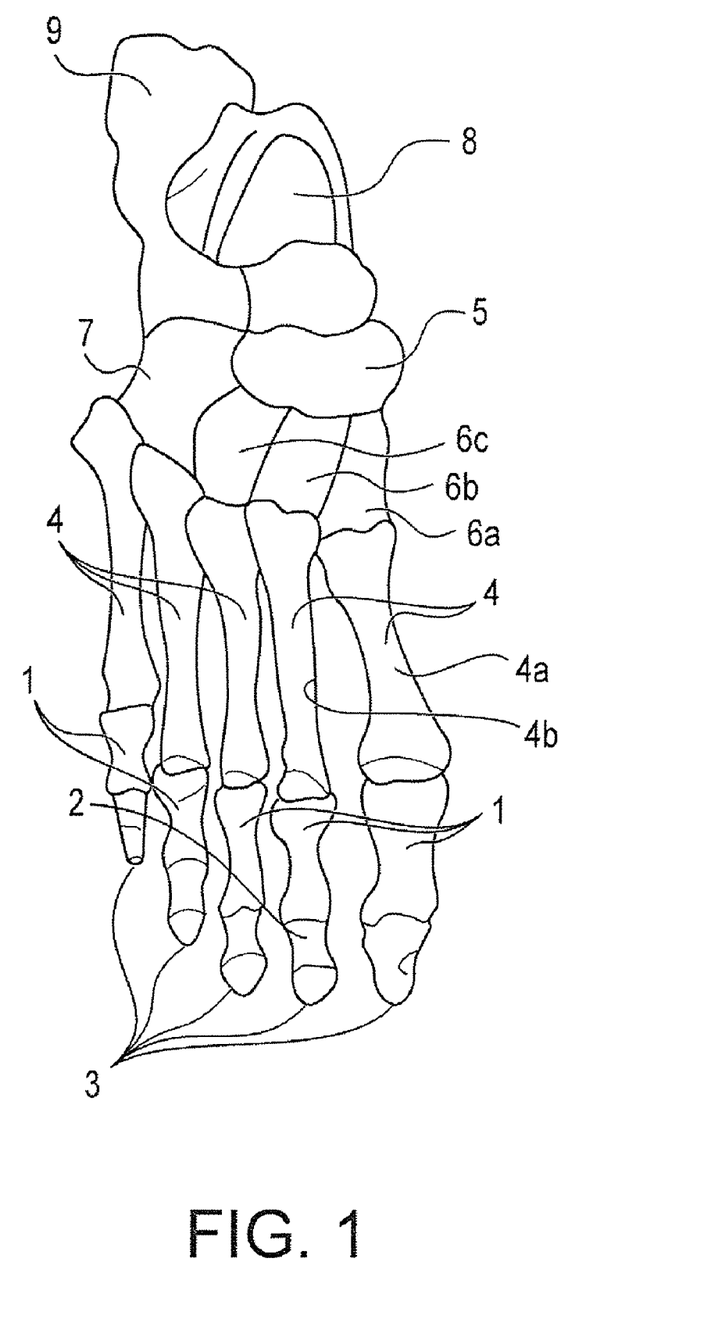
FIG. 1 illustrates a top view of foot bones.

Referring to FIG. 1, the foot has three main parts: the forefoot, the midfoot, and the hindfoot. The forefoot is composed of the five toes, called phalanges 1, 2, 3, and their connecting long bones, called metatarsals 4. Each toe, except the big toe, is made up of three phalanges—proximal phalange 1, middle phalange 2, and distal phalange 3—and two joints. The phalanges 1, 2, 3 are connected to the metatarsals 4 by the metatarsal phalangeal joints at the ball of the foot. The big toe has two phalanges—distal phalange 3, and proximal phalange 1—and a joint called the interphalangeal joint. The big toe articulates with the head of the first metatarsal 4a and is called the first metatarsophalangeal joint (MTPJ). Underneath the first metatarsal 4a head are two tiny, round bones called sesamoids.

The midfoot has five irregularly shaped tarsal bones—navicular 5, medial cuneiform 6a, intermediate cuneiform 6b, lateral cuneiform 6c, and cuboid 7. The bones of the midfoot are connected to the forefoot and the hindfoot by muscles and the plantar fascia called arch ligament.

The hindfoot is composed of the talus 8 (lower ankle) and calcaneus 9 (heel). The top of the talus 8 is connected to the tibia and fibula of the lower leg forming a hinge that allows the foot to move up and down. The calcaneus 9 joins the talus 8 to form the subtalar joint.

Tarsometatarsal articulations are arthrodial joints in the foot, also known as the "Lisfranc joint." The Lisfranc joint is the medial articulation involving the first 4a and second metatarsals 4b with the medial 6a and intermediate 6b cuneiforms. The Lisfranc ligament is a large band of plantar collagenous tissue that spans the articulation of the medial cuneiform 6a and the base of the second metatarsal 4b. A Lisfranc injury is an injury to the Lisfranc ligament which can occur as a result of direct or indirect trauma. Sometimes, the Lisfranc injury is a dislocation such as a ligament injury or a fracture and dislocation. The dislocation may be a separation of the joints between the forefoot and the midfoot. The fracture usually occurs in the midfoot bones.

The treatment of a Lisfranc injury is often surgical, though some minor injuries can be treated conservatively. In the case of a minimal displacement of the bones, a stiff walking cast applied for approximately eight weeks may suffice. However, the more common treatment is to secure the fractured and dislocated bones with internal or external fixation means.

Thus, there is a need for a Lisfranc repair technique that is simple, flexible and is performed by a minimally invasive lateral approach, with placement of buttons across the lateral margin of the medial cuneiform and the medial second metatarsal.

SUMMARY OF THE INVENTION

The present invention fulfills the needs noted above by providing a surgical procedure for Lisfranc repair using a suture-button construct with surgically useful qualities, including placement of buttons across the lateral margin of the medial cuneiform and the medial second metatarsal.

The surgical procedure of the present invention may be performed under local anesthesia, i.e., an injection of Liodocaine, Marcaine or Dexamethoasone. The suture-button construct of the present invention can be used to stabilize an injury of the Lisfranc ligament, attached to the lateral margin of the medial cuneiform and medial second metatarsal base, when used between the base of the second metatarsal and the medial cuneiform in the direction of the injured Lisfranc ligament.

The present invention includes a suture-button construct for use in Lisfranc repair formed of a pair of buttons connected by suture strand. The first button has two apertures while the second button has four apertures, the apertures to allow the passage of suture strand. A first suture strand is fed through the first aperture of the second button and through, in turn, the second and first apertures of the first button and through the second and fourth apertures of the second button and through, in turn, the second and first apertures of the first button and through the third aperture of the second button. A second suture strand looped through one of the first and second apertures of the first button and is operatively associated with a needle. Preferably, the first suture strand is double looped through the first and second buttons. The buttons may be formed, for example, of titanium, stainless steel, PolyEtherEther-Ketone (PEEK) or Poly-L Lactic Acid (PLLA). The suture strand may be FiberWire® suture strand, sold by Arthrex, Inc. of Naples, Fla.

The present invention also includes a method of fixation of Lisfranc using a suture-button construct. The method includes the steps of providing a suture-button construct as described above. A dorsal longitudinal incision, preferably about 5 mm, over medial border of the foot overlying the medial cuneiform is made. A cannulated guide wire is inserted from a medial aspect of the medial cuneiform into the base of the second metatarsal and a cannulated drill bit is passed over the guide wire to drill a hole in a medial cuneiform and through a second metatarsal base. Alternatively, a K-wire (Kirschner wire) may be used to drill the hole.

A pull-through needle with pull-through suture strand is passed into the drill hole from medial to lateral direction and a suture-button construct is placed across the second metatarsal and medial cuneiform. The pull-through suture strand is pulled and a lateral tension is simultaneously applied on a first suture strand such that a first button of the suture-button construct lies sideways for passage through the hole. The first button is advanced in the hole until it exits the hole at the medial aspect of the medial cuneiform. The first button is then flipped to engage it against the medial aspect of the medial cuneiform, a lateral tension is applied on the first suture strand, and the pull-through suture strand is cut and removed. Subsequently, the second button is tightened down over the second metatarsal base by pulling on the free ends of the first suture strand and the second button is secured against the second metatarsal base. The free ends of the first suture strand are tied using a surgeon's knot and two reverse half-hitches.

The surgical method of fixation of Lisfranc using a suture-button construct, as described in the earlier paragraph, may also be performed by having a first button seated against the medial aspect of the intermediate cuneiform and the second button against the second metatarsal base. Alternatively, the second button may be placed against the medial cuneiform and the first button against the lateral aspect of the second metatarsal base, distal to the articulation between the second and third metatarsals. In addition, there are several alternative reduction orientations including first metatarsal to second metatarsal, cuneiforms (first, second and third), and second metatarsal to second cuneiform.

One of the buttons used in the present invention has an oblong body with first and second apertures, each of the apertures being tapered and terminating in a respective apex, the respective apexes being directed away from each other and being located substantially about a longitudinal mid-line of the oblong body. Preferably, each aperture is substantially triangular in plan view. More preferably, each of the apertures has first, second and third sides and the first sides of the respective first and second apertures are substantially parallel. More preferably, the second and third sides of each aperture are of substantially the same length while being longer than the first side.

The first and second apertures of the oblong button can have any shape, provided that each aperture is tapered and terminates in a respective apex. In one preferred embodiment, the aperture is substantially triangular in plan view. In another embodiment, the aperture is an egg-shaped or oval aperture, the curved narrower end comprising the apex.

The suture-button construct of the present invention also includes a button with a round body having four apertures, each of the apertures being located substantially equidistant from the center of the round body. Preferably, each aperture is substantially round in plan view. Another embodiment is a cup-shaped button.

The round button may have any suitable dimension (diameter and thickness). For example, the round button may have a diameter of about 5.5 mm and a thickness of about 1.27 mm. The centers of the four apertures are about 1.27 mm from the center of the button and the centers of a first pair of apertures lie substantially along an axis passing through the center of the button. The axis connecting the centers of the remaining two apertures, i.e., a second pair of apertures, is substantially perpendicular to the axis connecting the centers of the first pair of apertures.

The apertures of the round button can have any shape, provided that each aperture is equidistant from the center of the round body. One preferred embodiment is an aperture, which is substantially round in plan view. Another embodiment is an egg-shaped or oval aperture.

The suture-button construct and the surgical technique of the present invention have several advantages over other existing apparatuses and surgical procedures: (1) typically, patients who undergo Lisfranc repair in accordance with the present invention are required to wear post-operation shoe or boot for about 4-5 weeks in comparison to about 8-12 weeks for patients who undergo other Lisfranc repair procedures; (2) post-operation morbidity for patients is significantly reduced; and (3) the suture-button construct provides great strength and security in comparison to a soft tissue repair.

These and other features and advantages of the present invention will become apparent from the following description of the invention that is provided in connection with the accompanying drawings and illustrated embodiments of the invention.

DETAILED DESCRIPTION OF THE PREFERRED EMBODIMENTS

The present invention is method and apparatus for Lisfranc repair, which utilizes a suture-button construct that is placed across the lateral margin of the medial cuneiform and medial second metatarsal.

Figure 2:
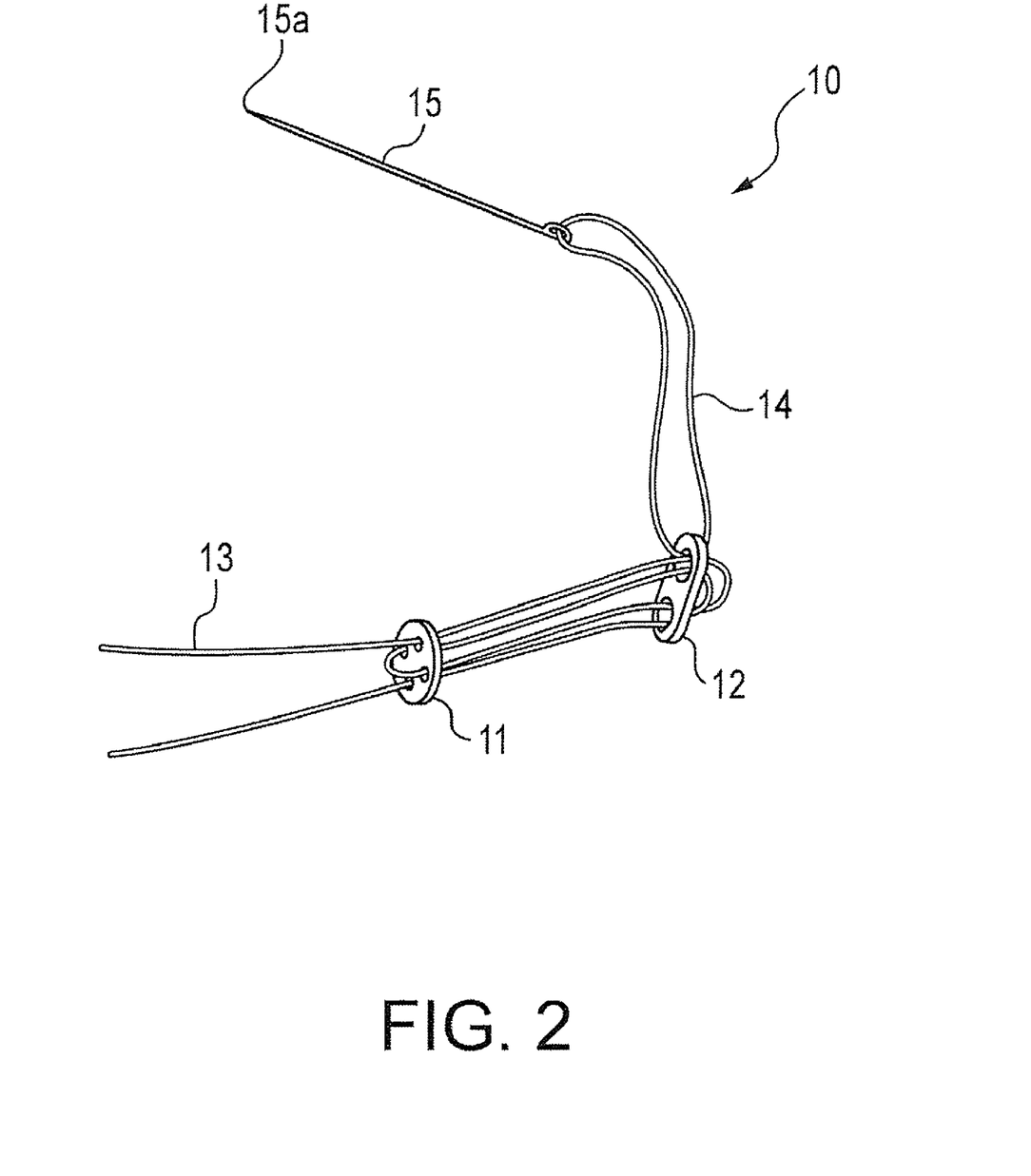
FIG. 2 illustrates a perspective view of assembled suture-button construct of the present invention.
Figure 3:
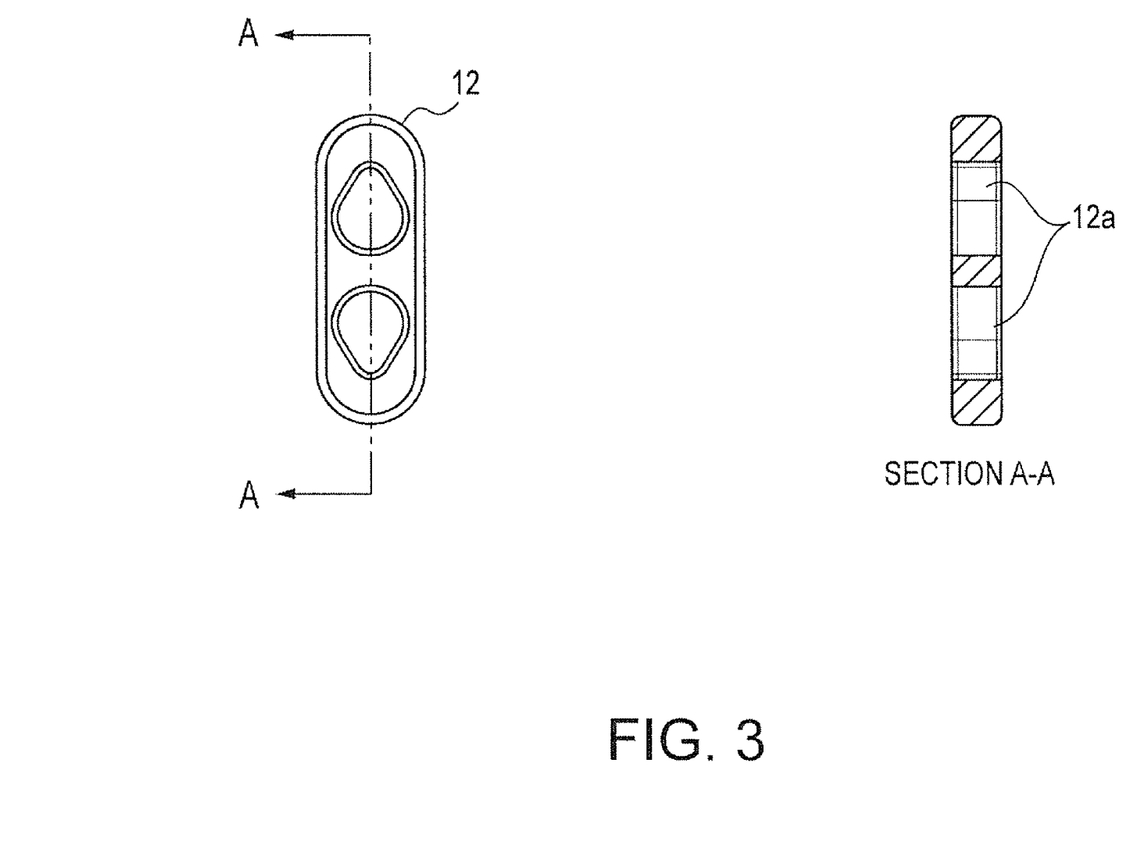
FIG. 3 illustrates a front, side, perspective view of a round button which forms part of the suture-button construct of the present invention.
Figure 4:
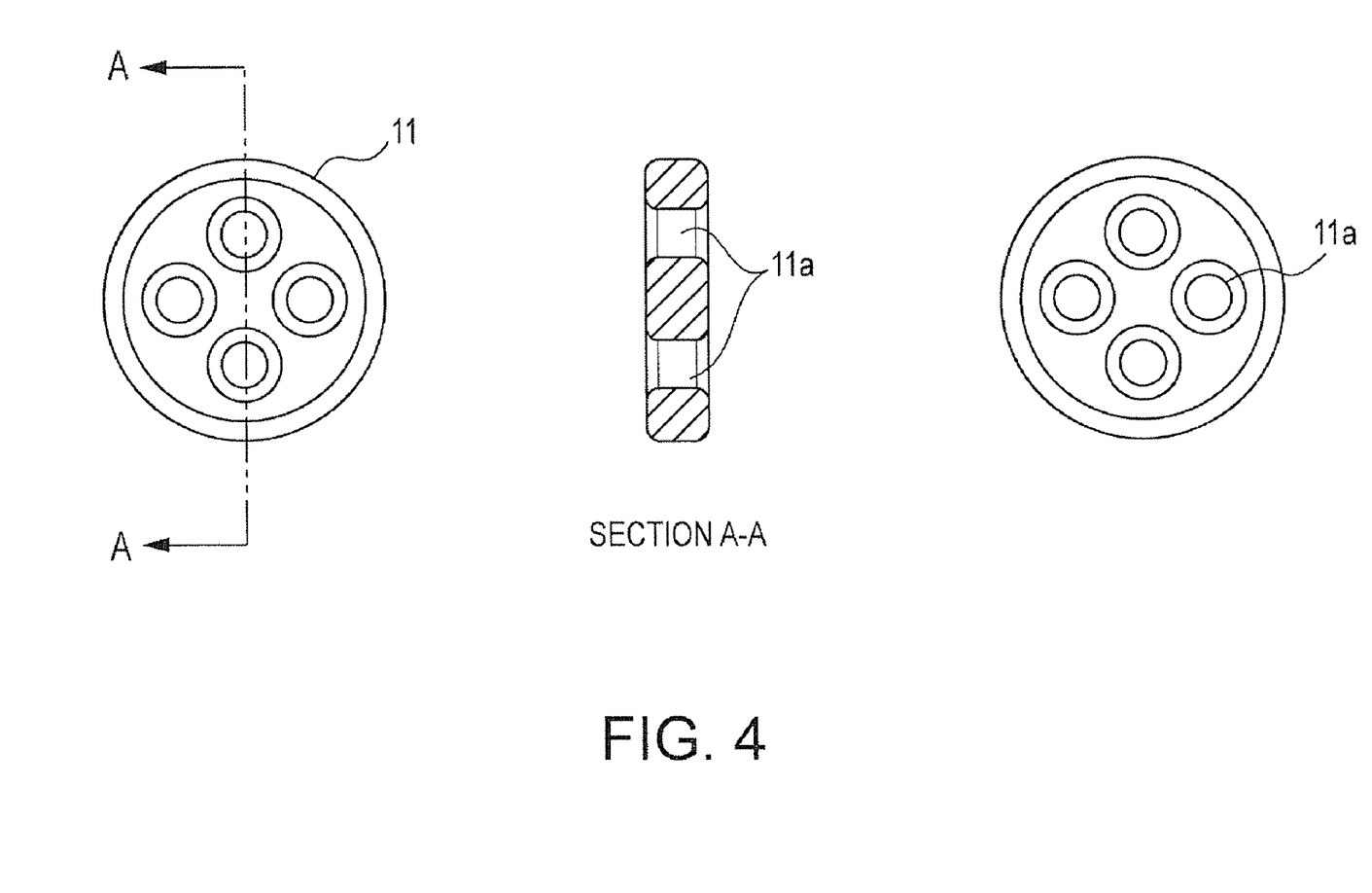
FIG. 4 illustrates a front, side, perspective view of an oblong button which forms part of the suture-button construct of the present invention.

Referring to FIG. 2, the suture-button construct 10 of the present invention is formed of a first button 12, a second button 11, a first suture strand 13 double looped through the apertures 11a (FIG. 3), 12a (FIG. 4) of the first button 11 and the second button 12. The suture-button construct 10 also includes a pull-through needle 15 with a pull-through suture strand 14 looped through an aperture 12a (FIG. 4) of the first button 12. The first button 12 is preferably oblong in shape (FIG. 4). The second button 11 is preferably round in shape (FIG. 3).

TABLE 1

| Apparatus of the present invention | |
|---|---|
| First Button | |
| Overall dimensions: | 8.0 mm (length) × 2.6 mm (width) × 1.3 mm (thickness) |
| Basic shape: | Oblong in plan shape, with chamfered or rounded corners and edges - this reduces the chance of the button being palpated under the skin and in addition, eases the passage of the first button through the drill hole as will be explained hereinafter |
| Button material: | Titanium, stainless steel, PEEK or PLLA |
| Button apertures: | 2 apertures (triangular in plan shape) |
| Aperture dimensions: | 2 mm base × 2 mm perpendicular height (equilateral triangle with chamfered corners), 1 mm distance between first and second apertures |
| Second Button | |
| Overall dimensions: | 5.5 mm (diameter) × 1.27 mm (thickness) |
| Basic shape: | Round in plan shape, with chamfered or rounded corners and edges |
| Button material: | Titanium, stainless steel, PEEK or PLLA |
| Button apertures: | 4 apertures (circular in plan shape), centers of the apertures at about 1.27 mm from the center of the button |

TABLE 1-continued

Apparatus of the present invention

| | |
|---|---|
| Aperture dimensions: | 0.95 mm (diameter) (free of burrs or sharp edges) |
| | First suture strand |
| Suture material: | #2 FiberWire ®, blue in color (FiberWire ® is made of ultra-high molecular weight polyethylene (UHMWPE) and polyester, braided over a UHMWPE core) |
| Suture use: | Looped twice through the first and second apertures of thef irst and second buttons, leaving the two free ends of suture strand free for tying |
| Pull-through needle | 127 mm long straight needle with pull-through suture strand attached |
| | Pull-through suture strand |
| Suture material: | #2 FiberWire ®, white in color |
| Suture use: | Looped once through an aperture of the first button, both free ends of pull-through suture strand being attached through the eye of the pull-through needle |
| Guidewire | 1.2 mm (diameter) |
| Cannulated Drill Bit | Stainless steel (material), 178 mm (length) × 2.7 mm (diameter), 1.35 mm cannulation for a guidewire to pass through |

The first suture strand 13 used in the present invention may be of any material, which is suitable for this purpose, whether absorbable or non-absorbable, provided it is sufficiently strong. A #2 FiberWire® suture strand, blue in color, is preferred. The #2 FiberWire® is a braided suture strand with an ultrahigh molecular weight polyethylene core and has almost twice the strength of a similarly sized generic suture strand. The #2 FiberWire® suture strand is a non-absorbable suture strand with increased abrasion-resistance, which knots easily without slipping.

The pull-through suture strand 14 used in the apparatus of the present invention may be formed of any suitable material, whether absorbable or non-absorbable, provided it is sufficiently strong. A #2 FiberWire® suture strand, white in color, is preferred.

The pull-through needle 15 may be of any dimensions, provided it is long enough to span the foot. The tip 15a of the pull-through needle 15 can be either "taper cut" or "cutting."

Figure 5:
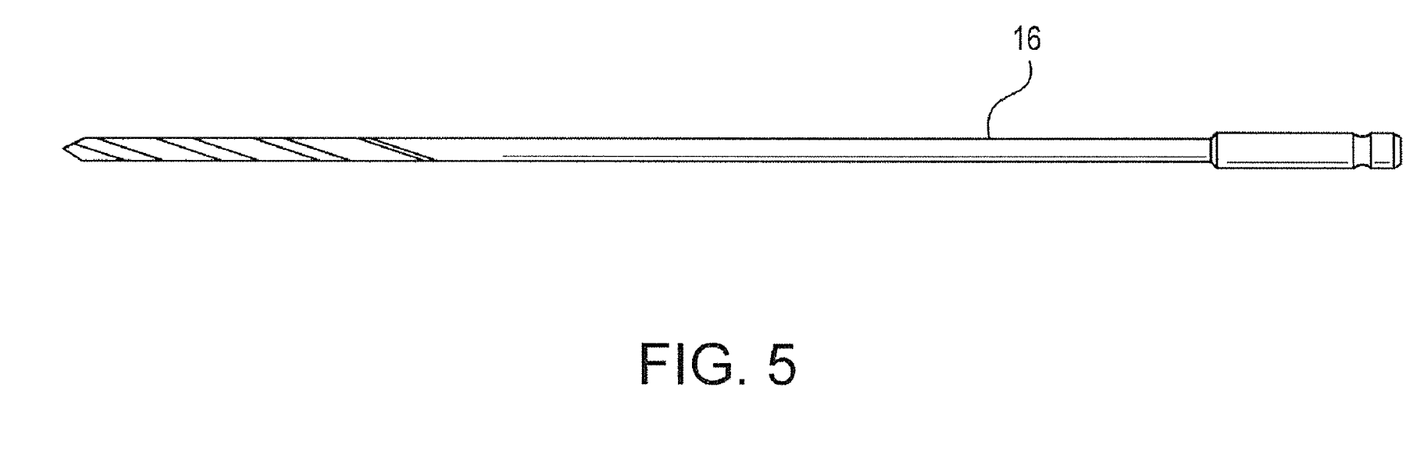
FIG. 5 illustrates a plan view of a cannulated drill bit used in the present invention.

Referring to FIG. 5, a cannulated drill bit 16, preferably a 2.7 mm drill bit, is used to drill a hole for the first suture strand 13 and the pull-through suture strand 14. Alternatively, a K-wire (Kirschner wire) may be used to drill the hole. The diameter of the hole must be sufficient to permit the first button 12 to be pulled, lengthways, thereto.

Surgical Technique

Figure 6A:
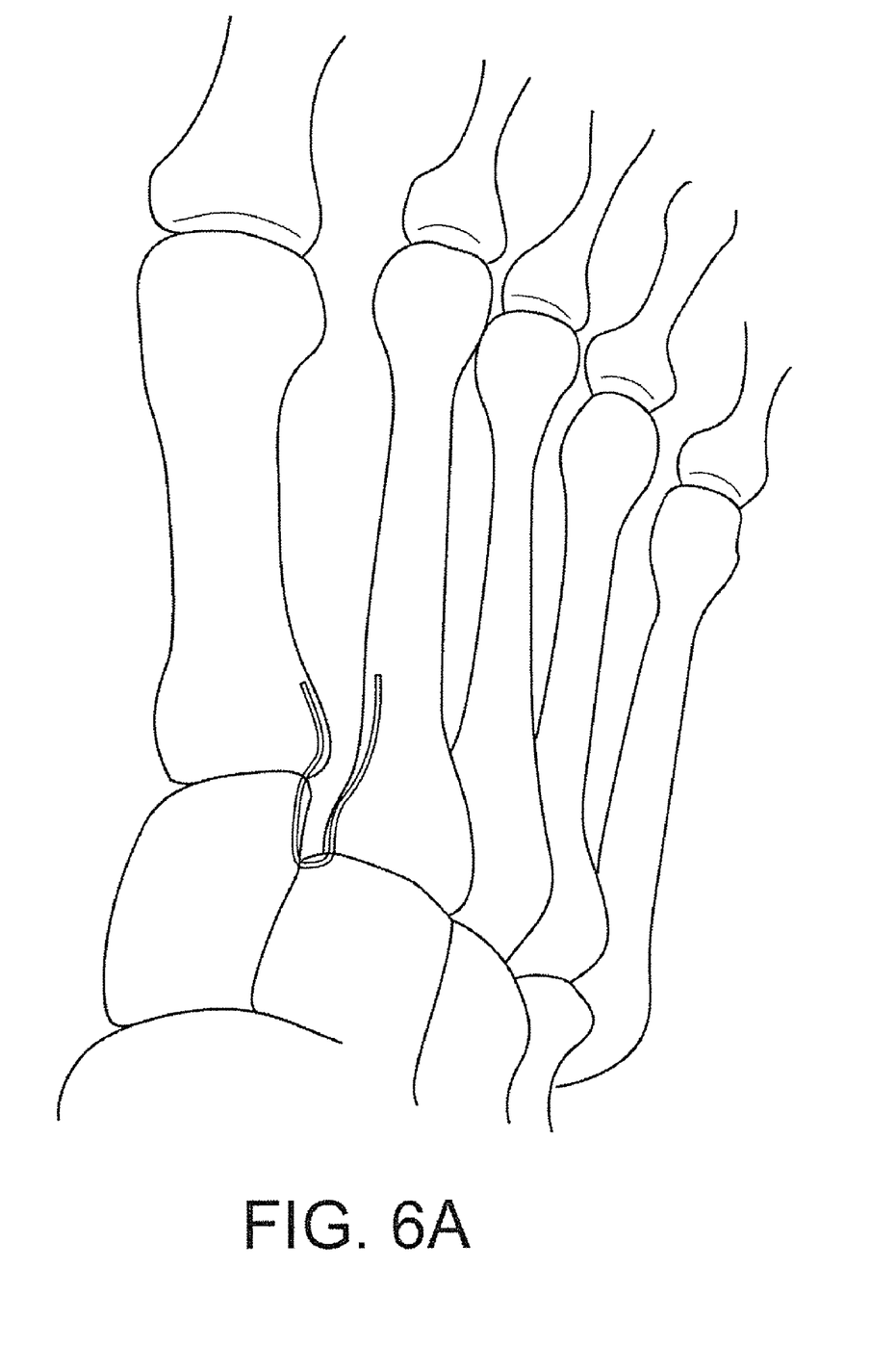
FIG. 6A shows a patient's foot with a Lisfranc injury, prior to performing a Lisfranc repair.
Figure 6B:
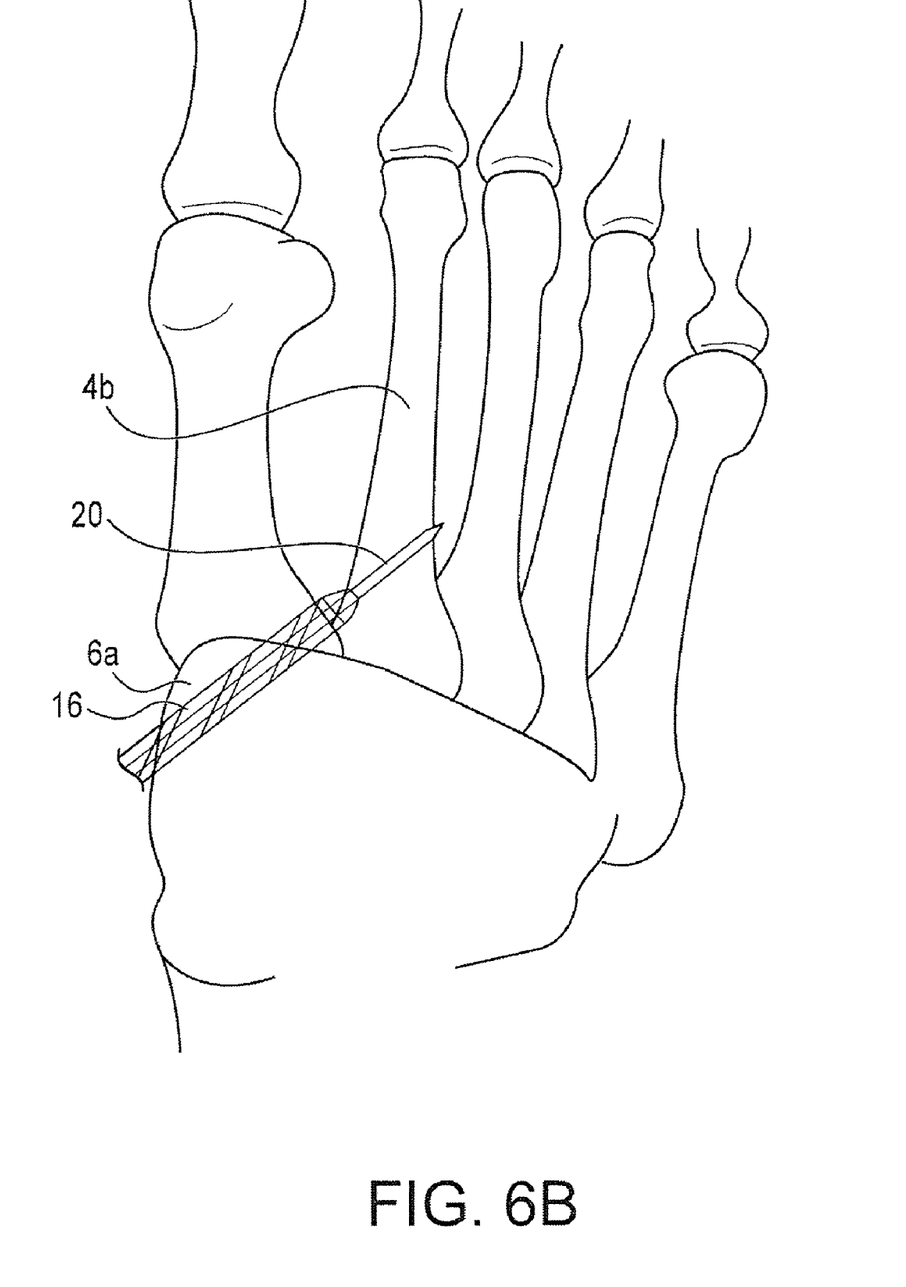
FIG. 6B illustrates a method of Lisfranc repair and shows a guidewire placed across the medial cuneiform and the second metatarsal base and a drill bit drilling a hole in the medial cuneiform and second metatarsal.

A patient's foot with a Lisfranc injury that needs a repair is shown in FIG. 6A. The surgical technique includes the following steps. First, a dorsal longitudinal incision, preferably about 5 mm, is made over medial border of the foot overlying the medial cuneiform 6a. Referring to FIG. 6B, a cannulated guide wire 20 is inserted from a medial aspect of the medial cuneiform 6a into the base of the second metatarsal 4b.

Next, a cannulated drill bit 16, preferably a 2.7 mm drill bit, is passed over the guide wire 20 to drill a hole. Alternatively, a K-wire (Kirschner wire) may be used to drill the hole. A pull-through needle 15 (FIG. 2), preferably a 1.2 mm guide pin, with a pull-through suture strand 14 (FIG. 2) is passed through the hole such that the pull-through needle 15 (FIG. 2) exits out of the medial aspect of the medial cuneiform 6a.

The pull-through suture strand 15 (FIG. 2) is pulled and a lateral tension is simultaneously applied on a first suture strand 13 (FIG. 6D) such that a first button 12 (FIG. 2) of the construct lies sideways for passage through the hole. The first button 12 (FIG. 2) of the construct is then advanced through the hole until it exits the hole at the medial aspect of the medial cuneiform 6a.

Figure 6C:
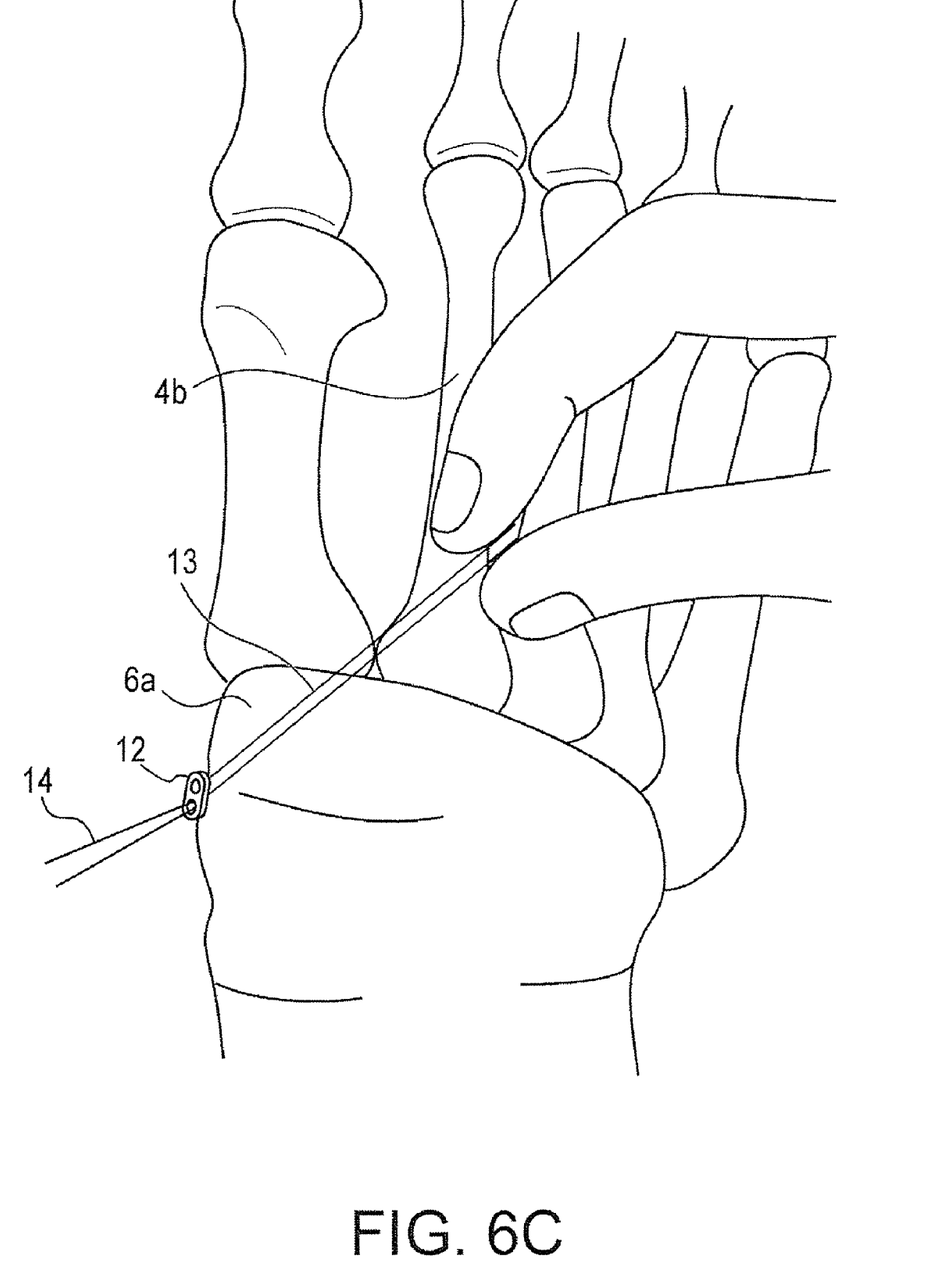
FIG. 6C illustrates a stage subsequent, although not immediate, to that shown in FIG. 6B and shows the first button of the construct exiting the hole on the medial side of the medial cuneiform.

Referring to FIG. 6C, once the first button 12 of the construct has exited the hole on the medial aspect of the medial cuneiform 6a, the angle of traction on the pull-through suture strand 14 is changed. A lateral tension is applied on the first suture strand 13 (FIG. 3D) to seat the first button 12 against the medial cuneiform 6a. The pull-through suture strand 14 is cut and removed. The surgeon may then manually push the medial cuneiform and the second metatarsal to correct any positioning.

Figure 6D:
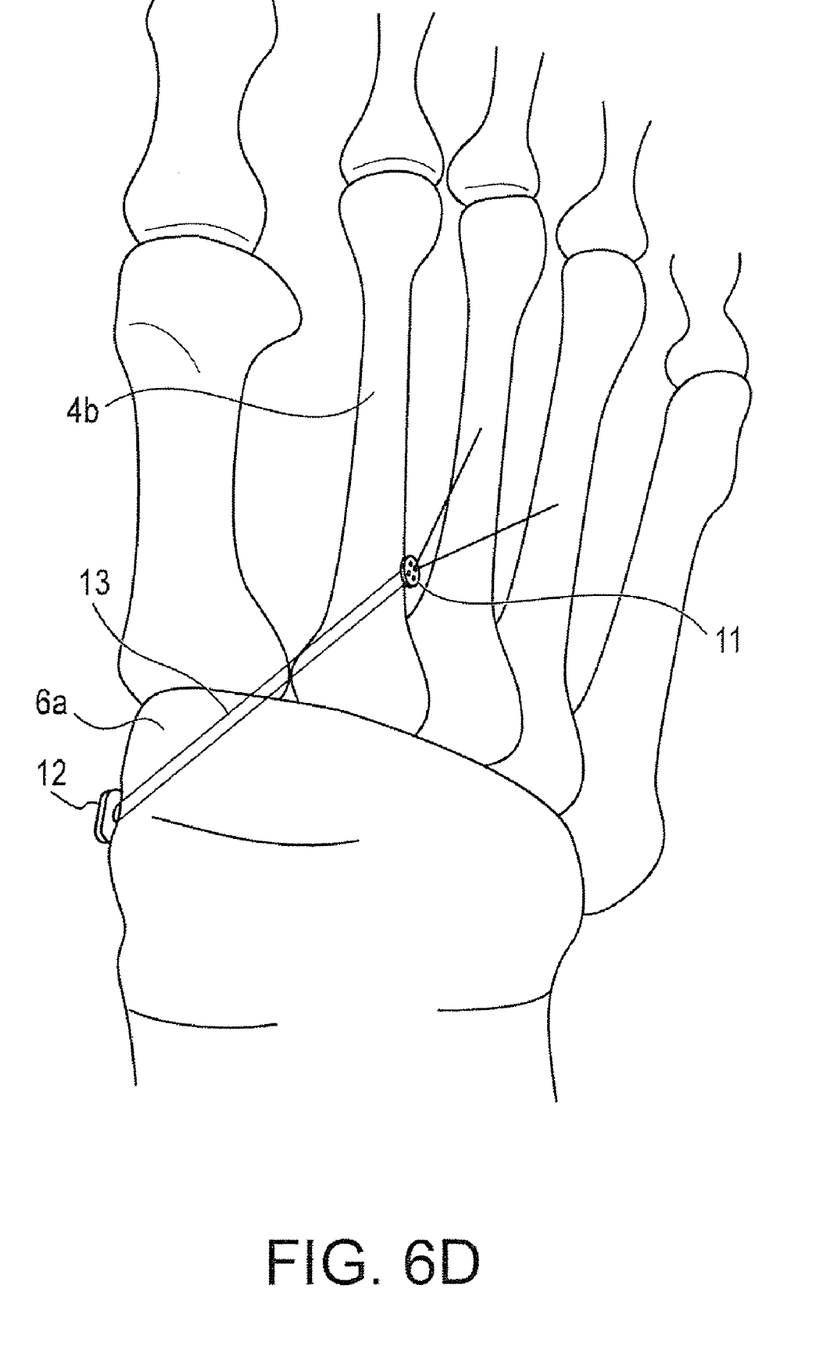
FIG. 6D illustrates a stage subsequent to that shown in FIG. 6C and shows the second button of the construct being seated down on the second metatarsal base.

Subsequently, as shown in FIG. 6D, the free ends of the first suture strand 13 are pulled to advance the second button 11 of the construct over the base of the second metatarsal 4b and to exert further traction on the free ends of the first suture strand 13 to engage the second button 11 against the base of the second metatarsal 4b. The free ends of the first suture strand 13 are tied by making a surgeon's knot and two reverse half-hitches.

Figure 6E:
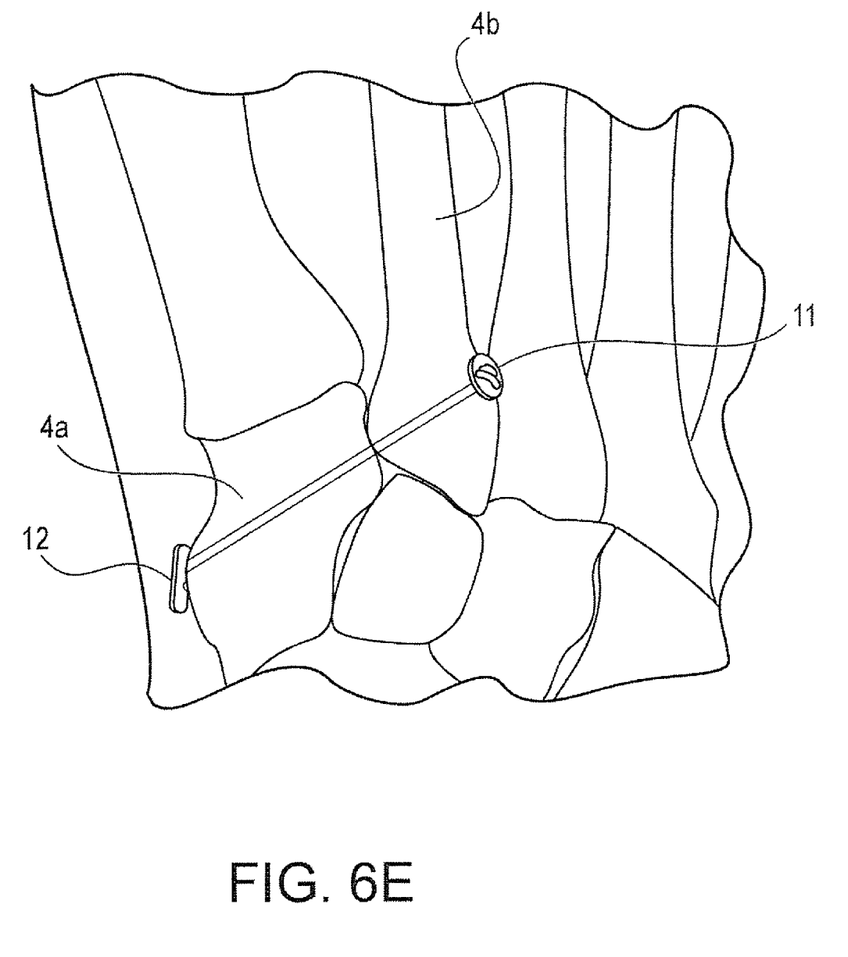
FIG. 6E illustrates a stage subsequent to that shown in FIG. 6D and shows the seating of two buttons of the construct, one each against the medial cuneiform and the second metatarsal base.

The first suture strand tails can be sewn to minimize the knot stack. Any remaining first suture strand is removed by cutting and pulling them out of the first and second buttons of the construct. At the end of the procedure, as shown in FIG. 6E, two buttons 11, 12 of the construct, one each against the medial cuneiform 6b and the second metatarsal base 4a hold the Lisfranc joint together.

The surgical method of fixation of Lisfranc using a suture-button construct, as described in the earlier paragraph, may also be performed by having a first button seated against the medial aspect of the intermediate cuneiform and the second button against the second metatarsal base. Alternatively, the second button may be placed against the medial cuneiform and the first button against the lateral aspect of the second metatarsal base, distal to the articulation between the second and third metatarsals. In addition, there are several alternative reduction orientations including first metatarsal to second metatarsal, cuneiforms (first, second and third), and second metatarsal to second cuneiform.

In another embodiment of the present invention, the suture-button construct is formed of a button, preferably a cup button, at one end, and a fully thread suture anchor at the other end. The suture anchor is inserted through a preformed hole from medial aspect of the medial cuneiform 6a into a preformed hole in the base of the second metatarsal 4b, and screwed into place in the second metatarsal 4b. The cup button is then advanced and secured against the medial aspect of the medial cuneiform 6a by tying the free ends of the suture strand passing through the apertures of the cup button.

Implant Removal

Routine removal of the suture-button construct is typically not required. If, for any reason, the buttons need to be removed, they can be performed simply by small incisions over the first and the second button, cutting the first suture strand as it loops through the buttons and removing both the first and second buttons and the first suture strand.

Post Operation

Following the Lisfranc repair using the suture-button construct of the present invention, the patient's foot is placed in a soft dressing and the patient is allowed to bear weight with a walking boot or a postoperative stiff sole shoe. The patient is recommended to change the dressing weekly until suture removal at week two or three. Most patients are allowed to wear a comfortable shoe with a wide toebox about 4-5 weeks subsequent to the Lisfranc repair procedure as illustrated above.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed is:

1. A method of Lisfranc repair comprising:
   drilling a hole in a medial cuneiform and through a second metatarsal base;
   passing a needle with a pull-through suture strand of a suture-button construct through the hole, the needle entering the hole from the second metatarsal base and exiting the hole out of the medial cuneiform;
   pulling the pull-through suture strand and simultaneously applying a lateral tension on a first suture strand of the suture-button construct such that a first button of the suture-button construct lies sideways, and advancing the first button through the hole until the first button exits the hole at the medial cuneiform;
   flipping the first button to engage the first button against the medial aspect of the medial cuneiform and applying a lateral tension on the first suture strand;
   pulling free ends of the first suture strand of the suture-button construct to advance a second button of the suture-button construct over the second metatarsal base and to engage the second button against the second metatarsal base; and
   securing the second button against the second metatarsal base.

2. The method of claim 1, wherein the first button is oblong-shaped having at least two apertures, the at least two apertures being substantially triangular in shape.

3. The method of claim 1, wherein the second button is round-shaped having at least four apertures, the at least four apertures being substantially circular-shaped and centers of the at least four apertures being substantially equi-distant from a center of the second button.

4. The method of claim 1, wherein the first suture strand and the pull-through suture strand comprise a plurality of fibers of ultrahigh molecular weight polyethylene.

5. The method of claim 1, further comprising the initial step of making a dorsal longitudinal incision over medial border of foot overlying medial cuneiform.

\* \* \* \* \*